(12) United States Patent
Matsumoto et al.

(10) Patent No.: US 8,381,387 B2
(45) Date of Patent: Feb. 26, 2013

(54) METHOD OF FABRICATING AN ULTRASONIC TRANSDUCER

(75) Inventors: Kazuya Matsumoto, Nagano (JP); Ryo Ohta, Nagano (JP); Mamoru Hasegawa, Nagano (JP); Hideo Adachi, Iruma (JP); Katsuhiro Wakabayashi, Hachioji (JP)

(73) Assignees: Olympus Medical Systems Corp., Tokyo (JP); Olympus Corporation, Tokyo (JP)

(*) Notice: Subject to any disclaimer, the term of this patent is extended or adjusted under 35 U.S.C. 154(b) by 149 days.

(21) Appl. No.: 12/914,651

(22) Filed: Oct. 28, 2010

(65) Prior Publication Data

US 2011/0036808 A1 Feb. 17, 2011

Related U.S. Application Data

(62) Division of application No. 11/870,786, filed on Oct. 11, 2007, now Pat. No. 7,952,256.

(30) Foreign Application Priority Data

Oct. 11, 2006 (JP) .................................. 2006-278043
Oct. 9, 2007 (JP) .................................. 2007-263696

(51) Int. Cl.
*H04R 31/00* (2006.01)
*H04R 17/00* (2006.01)
*H01L 41/22* (2006.01)

(52) U.S. Cl. ............. 29/594; 29/25.35; 29/846; 216/39; 438/42

(58) Field of Classification Search .................... 29/594, 29/25.35, 842, 846, 830, 852; 310/309, 334; 216/13, 39; 438/42, 200
See application file for complete search history.

(56) References Cited

U.S. PATENT DOCUMENTS

| 5,982,709 | A | 11/1999 | Ladabaum et al. |
| 7,257,051 | B2 | 8/2007 | Thomenius et al. |
| 7,280,435 | B2 | 10/2007 | Thomenius et al. |
| 7,408,283 | B2 | 8/2008 | Smith et al. |
| 7,489,593 | B2 | 2/2009 | Nguyen-Dinh et al. |
| 7,770,279 | B2 | 8/2010 | Nguyen-Dinh et al. |
| 2003/0032211 | A1 * | 2/2003 | Ladabaum ........... 438/42 |

FOREIGN PATENT DOCUMENTS

JP 2004120764 A * 4/2004

* cited by examiner

*Primary Examiner* — A. Dexter Tugbang
(74) *Attorney, Agent, or Firm* — Scully Scott Murphy & Presser, PC

(57) ABSTRACT

An ultrasonic transducer fabrication method including: depositing a conductive material on an insulating layer, partially etching the conductive material to form lower electrodes; depositing an insulating material to cover the lower electrodes to form a first insulating layer and depositing a sacrificial material thereon, performing etching, to create cavities and a channel-shaped sacrificial layer to communicate the cavities; depositing an insulating material on the first insulating layer to form a second insulating layer; partially etching the second insulating layer to form holes; etching and removing the sacrificial layer through the holes to form the cavities and channels; depositing a conductive material on the second insulating layer to plug the holes and form a conductive film; partially etching the conductive film to form upper electrodes and sealing portions which plug the holes; and forming a protective film on the second insulating layer to cover the upper electrodes and the sealing portions.

4 Claims, 12 Drawing Sheets

METHOD OF FABRICATING AN ULTRASONIC TRANSDUCER

This application is a divisional application of U.S. application Ser. No. 11/870,786 filed on Oct. 11, 2007, now U.S. Pat. No. 7,952,256, which claims benefit of Japanese Application Nos. 2006-278043 filed on Oct. 11, 2006 and 2007-263696 filed on Oct. 9, 2007, the entire contents of each of which are incorporated herein by reference.

BACKGROUND OF THE INVENTION

1. Field of the Invention

The present invention relates to a capacitive type ultrasonic transducer, a fabrication method for the ultrasonic transducer, and an ultrasonic endoscope which has the ultrasonic transducer in an ultrasonic transmission and reception portion.

2. Description of the Related Art

To form cavities in an ultrasonic transducer, a method is known which creates cavities and channels communicating the cavities with each other by using a sacrificial layer, forms an insulating layer on the sacrificial layer, creates holes in the insulating layer, pours a chemical agent or gas to dissolve the sacrificial layer, and thereby removes the sacrificial layer. This method can form cavities under the insulating layer. Besides, it is necessary to form sealing portions to prevent holes for subsequent processes. With conventional techniques, however, material used to form the sealing portions is deposited in the cavities more than necessary, distorting shape of the sealing portions. This makes shape of the cavities non-uniform.

U.S. Pat. No. 5,982,709A discloses a fabrication technique for an ultrasonic transducer in which channels for removal of a sacrificial layer are formed in membrane support posts along a substrate surface. The ultrasonic transducer can avoid deposition of film-forming member in cavities during a CVD (Chemical Vapor Deposition) based film formation process for forming sealing portions intended to plug sacrificial layer removal holes made in the membrane support posts and can prevent vibration of membranes from being hindered.

That is, the ultrasonic transducer disclosed in U.S. Pat. No. 5,982,709A prevents the film-forming member from entering the cavities using a crank-shaped (T-shaped) geometry for the channels running from the sealing portions to the cavities, where the sealing portions are created by forming a film in the sacrificial layer removal holes by CVD.

SUMMARY OF THE INVENTION

An ultrasonic transducer according to the present invention comprises: two or more ultrasonic transducer cells, each of which includes a lower electrode, a first insulating layer placed on the lower electrode, a cavity placed on the first insulating layer, a second insulating layer placed on the cavity, and an upper electrode placed above the second insulating layer; channels which communicate the cavities with each other; the second insulating layer placed on the channels; holes formed in the second insulating layer placed on the channels; and sealing portions which seal the holes, where that part of the sealing portions which enters the channels is the same in cross-sectional shape as the holes.

An ultrasonic transducer fabrication method according to the present invention comprises the steps of: depositing a conductive material on an insulating layer on a surface of a substrate, partially etching the conductive material, and thereby forming lower electrodes; depositing an insulating material so as to cover the lower electrodes and the insulating layer and thereby forming a first insulating layer; depositing a sacrificial material on the first insulating layer, performing etching, and thereby creating two or more cavities and a channel-shaped sacrificial layer which communicates the cavities with each other; depositing an insulating material on the first insulating layer and the sacrificial layer and thereby forming a second insulating layer; partially etching the second insulating layer formed on the channel-shaped sacrificial layer and thereby forming holes; etching and removing the sacrificial layer through the holes and thereby forming the cavities and the channels; depositing a conductive material on the second insulating layer by a vacuum evaporation or a sputtering process so as to plug the holes, further depositing a conductive material by a chemical vapor deposition, and thereby forming a conductive film; partially etching the conductive film and thereby forming upper electrodes and sealing portions which plug the holes; and forming a protective film on the second insulating layer using a protective material so as to cover the second electrodes and the sealing portions.

An ultrasonic endoscope according to the present invention has an ultrasonic transducer at a distal end of a distal end rigid portion that makes up a distal end of an endoscope insertion portion, the ultrasonic transducer comprising: two or more ultrasonic transducer cells, each of which includes a lower electrode, a first insulating layer placed on the lower electrode, a cavity placed on the first insulating layer, a second insulating layer placed on the cavity, and an upper electrode placed above the second insulating layer; channels which communicate the cavities with each other; the second insulating layer placed on the channels; holes formed in the second insulating layer placed on the channels; and sealing portions which seal the holes, where that part of the sealing portions which enters the channels is the same in cross-sectional shape as the holes.

The above and other objects, features and advantages of the invention will become more clearly understood from the following description referring to the accompanying drawings.

DETAILED DESCRIPTION OF PREFERRED EMBODIMENTS

Conventionally known ultrasonic transducers have a problem in that channels for removal of a sacrificial layer have complicated shapes, complicating the process for forming the channels as well. Such channel shapes can result in longer etching time for removal of the sacrificial layer, making it likely that membrane member will be etched unnecessarily.

That is, since an etching rate of a sacrificial layer depends on channel length, it takes a long sacrificial layer removal time to form channels of a conventional shape. Consequently, part of other insulating layers may be removed as well, distorting shape of cavities, thereby making membrane structures non-uniform, and thus obstructing vibration generation of membranes.

This presents a problem in that membrane member of ultrasonic transducer cells, which require high accuracy, may vary in thickness depending on manufacturing processes, causing variation in vibration of the ultrasonic transducer cells. Thus, conventional ultrasonic transducers have a problem in that they cannot deliver ultrasonic vibration with high accuracy.

The conventional technique uses rectangular channels to increase channel length up to cavities, thereby preventing the CVD film used to plug sacrificial layer removal holes from being deposited in cavities. Ultrasonic transducers of such a configuration need to provide sufficient distance between cavities to increase the channel length. This makes it impossible to arrange a plurality of ultrasonic transducer cells in a single transducer element at high density, and thus impossible to deliver ultrasonic vibration to an ultrasonic scanning region with high accuracy. Consequently, internal bodily conditions are acquired as low-accuracy images from echo signals.

Furthermore, conventional ultrasonic transducer structure has disadvantages, including inability to make etching holes large enough to increase the channel length, making it impossible to increase the etching rate. Moreover, the need to form complicated channels poses an obstacle to refinement of two-dimensional sizes of the ultrasonic transducers.

Thus, by controlling shape of sealing portions of an ultrasonic transducer, a technique according to an embodiment described below brings shapes of multiple cavities close to uniformity, making it possible to generate ultrasonic vibration with high accuracy in a stable manner.

Now, embodiments of the present invention will be described below with reference to the drawings. Incidentally, the embodiments of the present invention will be described by taking as an example an ultrasonic endoscope which is a medical device. However, the ultrasonic endoscopes to which the ultrasonic transducer according to the present invention is applied are not limited to the one described below. Also, application of the ultrasonic transducer according to the present invention is not limited to ultrasonic endoscopes.

Figure 1:
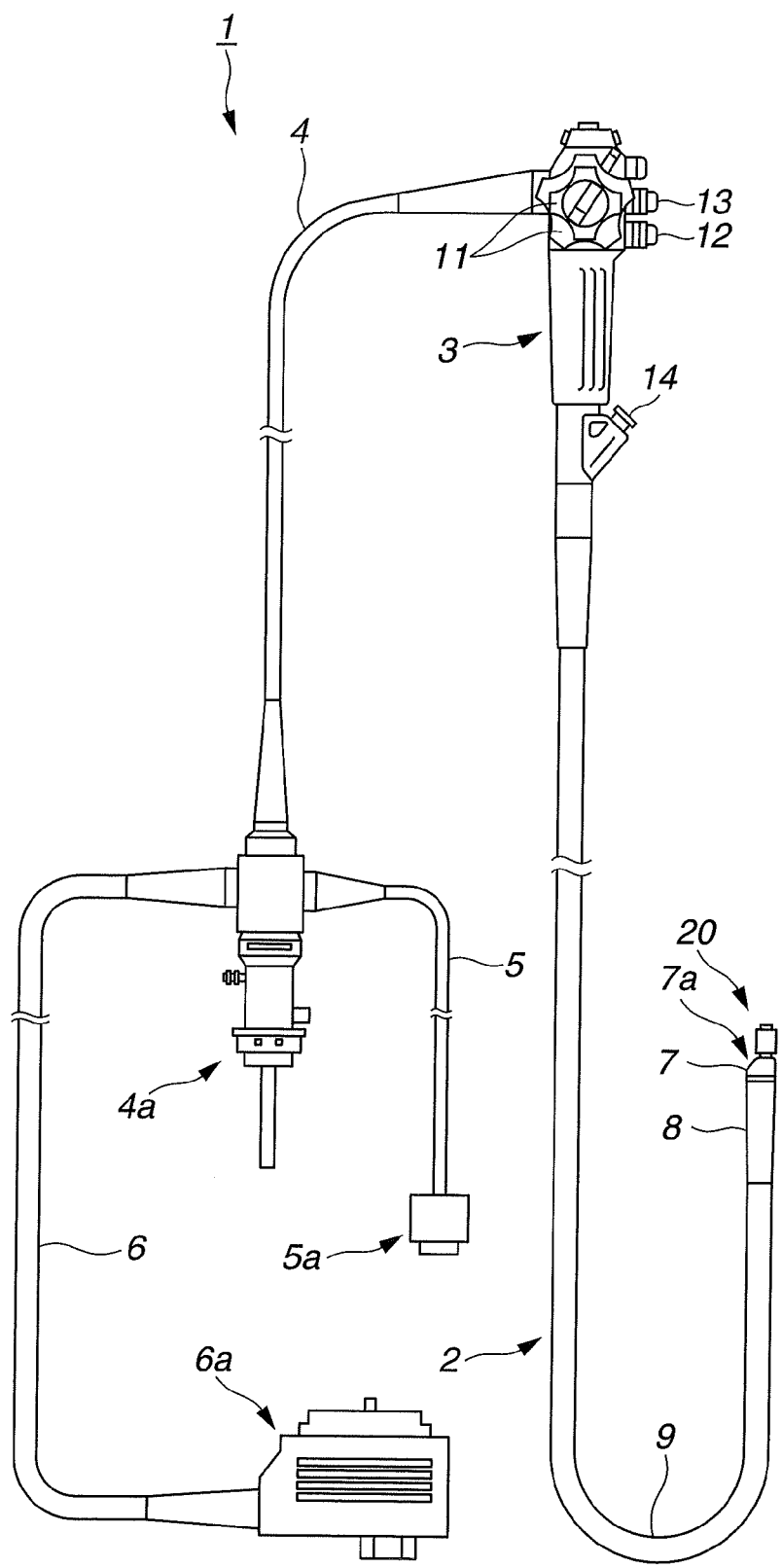
FIG. 1 is a diagram outlining a configuration of an ultrasonic endoscope according to a first embodiment of the present invention.
Figure 2:
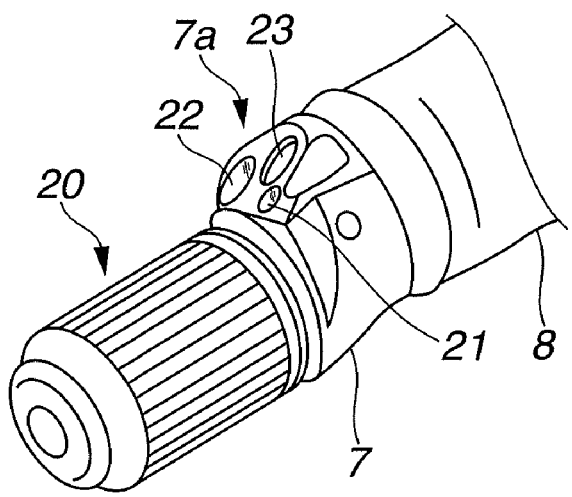
FIG. 2 is a diagram outlining a configuration of a distal end portion of the ultrasonic endoscope.
Figure 3:
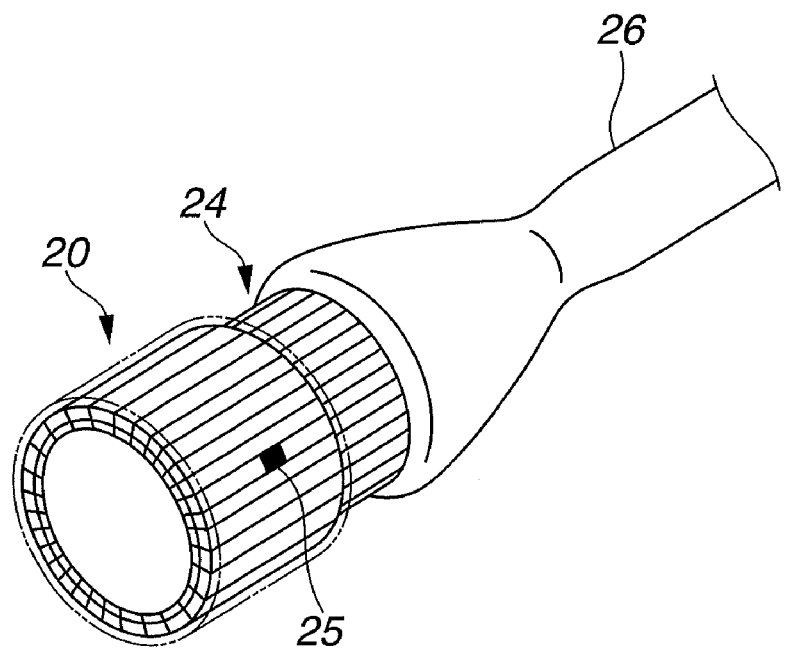
FIG. 3 is a diagram illustrating a configuration of an ultrasonic transducer portion.

An ultrasonic endoscope to which the ultrasonic transducer according to the present invention can be applied will be described with reference to FIGS. 1 to 3. FIG. 1 is a diagram outlining a configuration of the ultrasonic endoscope, FIG. 2 is a diagram outlining a configuration of a distal end portion of the ultrasonic endoscope, and FIG. 3 is a diagram illustrating a configuration of an ultrasonic transducer portion. However, components, shapes of the components, size ratios among the components, placement locations of the components, and the like of the ultrasonic endoscopes to which the ultrasonic transducer according to the present invention can be applied are not limited to those shown in the figures.

As shown in FIG. 1, the ultrasonic endoscope 1 according to the present invention, which is a medical device, mainly includes a slender insertion portion 2 which is inserted into a body, an operation portion 3 located at a proximal end of the insertion portion 2, and a universal cord 4 which extends from a flank of the operation portion 3.

A proximal end portion of the universal cord 4 is equipped with an endoscope connector 4a for use to connect to a light source (not shown). An electrical cable 5 detachably connected to a camera control unit (not shown) via an electrical connector 5a as well as an ultrasonic cable 6 detachably connected to an ultrasonic observation apparatus via an ultrasonic connector 6a extend from the endoscope connector 4a.

Starting from the distal end, the insertion portion 2 comprises a distal end rigid portion 7, a bendable, bending portion 8 located at a rear end of the distal end rigid portion 7, and a small-diameter, long, flexible tubular portion 9 located at a rear end of the bending portion 8 and extending to a distal end portion of the operation portion 3, all of which are installed in a connected row arrangement. Then, an ultrasonic transducer portion 20 which includes an array of multiple electronic-scanning ultrasonic transducers used to transmit/receive ultrasound is installed at the distal end of the distal end rigid portion 7, making up an ultrasonic transmission and reception portion.

Regarding material of the distal end rigid portion 7, a rigid, chemical resistant, biocompatible material is preferable. Materials with such properties include, for example, polysulfone. The operation portion 3 has an angle knob 11 used to bend the bending portion 8 in a desired direction, air/water supply button 12 for air supply and water supply operations, suction button 13 for suction operations, and treatment instrument insertion port 14 which provides an entrance for treatment instruments introduced into the body and the like.

A distal end face 7a of the distal end rigid portion 7 where the ultrasonic transducer portion 20 is installed may also be provided, for example, as shown in FIG. 2, with an illumination lens cover 21 of an illumination optical system, observation lens cover 22 of an observation optical system, forceps port 23 which also serves as a suction port, and air/water supply nozzle (not shown).

The ultrasonic transducer portion 20 includes transducer elements 25. The transducer elements will be described later. FIG. 3 illustrates a distal end portion which includes an electronic radial transducer made up of multiple transducer elements 25 arranged in a cylindrical pattern. However, the ultrasonic transducer according to the present invention can be applied not only to the distal end portion of electronic radial ultrasonic endoscopes, but also to a convex distal end portion.

The ultrasonic transducer portion 20 has a cable connection substrate 24 installed in a connected row arrangement at a proximal end, the cable connection substrate 24 being equipped with an electrode pad electrically connected with the transducer elements 25 and a GND (ground) electrode pad. A coaxial cable bundle 26 whose signal lines are electrically connected to the cable connection substrate 24 extends from the ultrasonic transducer portion 20. The coaxial cable bundle 26 is passed through the distal end rigid portion 7, bending portion 8, flexible tubular portion 9, operation portion 3, universal cord 4, and ultrasonic cable 6 and connected to an ultrasonic observation apparatus (not shown) via an ultrasonic connector 6a.

Incidentally, application electrodes between the transducer elements 25 are supplied individually with electrical signals from respective cables in the coaxial cable bundle 26. That is, the application electrodes between the transducer elements 25 are electrically unconnected with each other.

First Embodiment

The ultrasonic transducer according to the present invention will be described below with reference to FIGS. 4 to 19.

Figure 4:
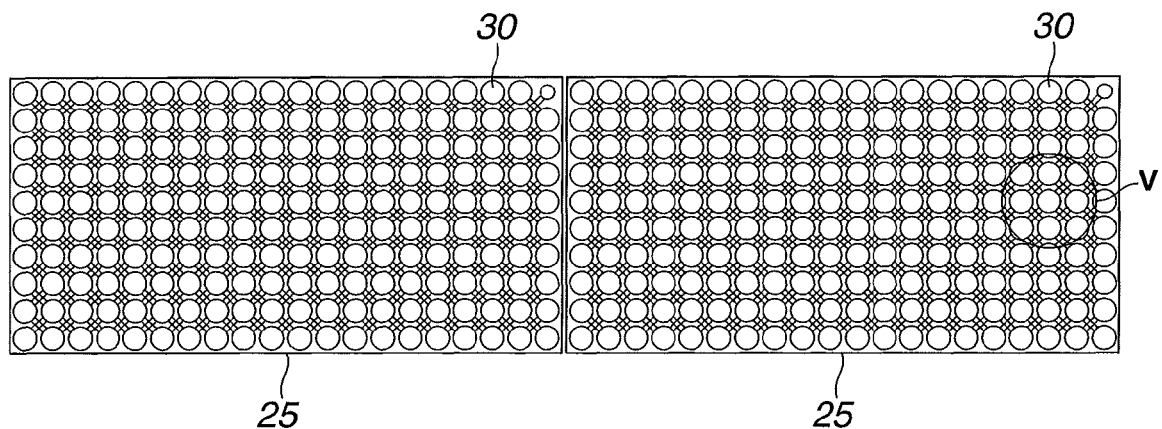
FIG. 4 is a top view of an ultrasonic transducer.
Figure 5:
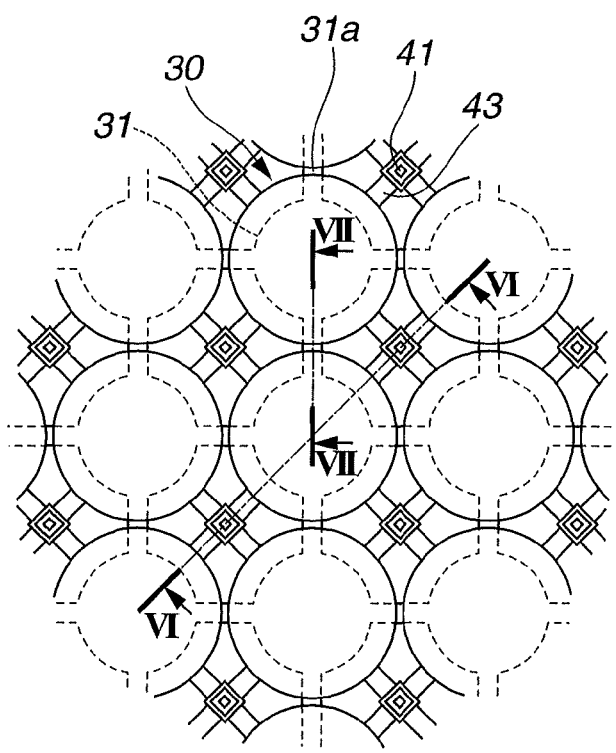
FIG. 5 is an enlarged view of encircled part V in FIG. 4.
Figure 6:
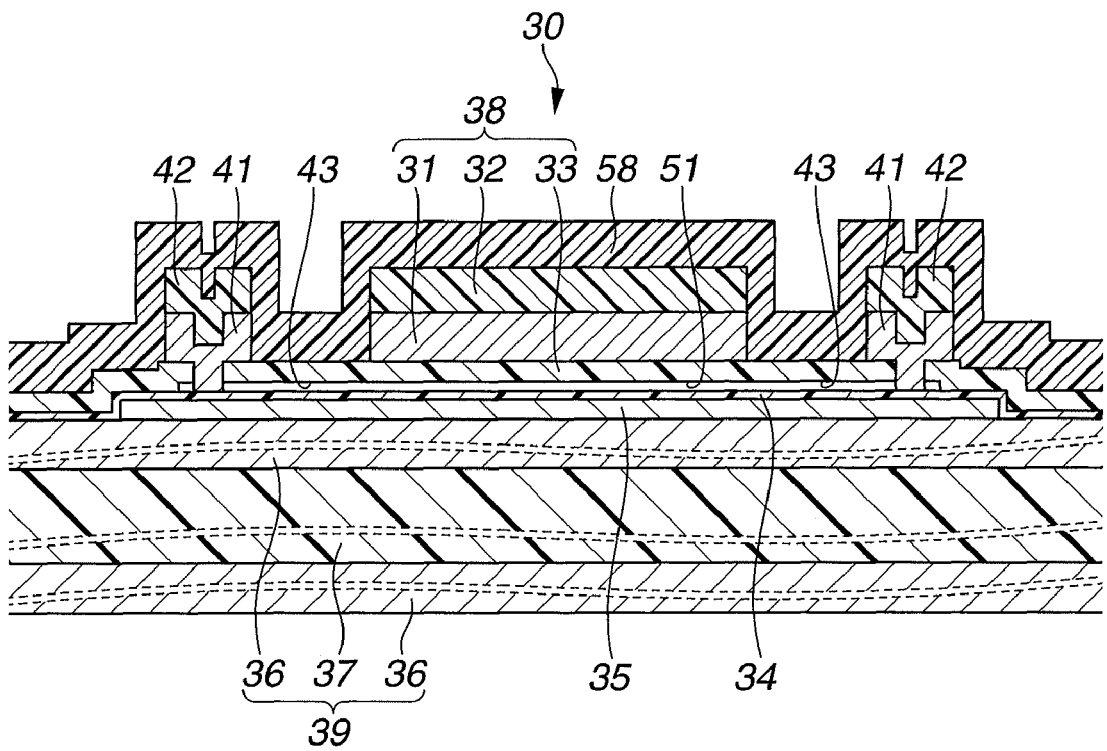
FIG. 6 is a partial cross-sectional view of ultrasonic transducer cells taken along VI-VI line in FIG. 5.
Figure 7:
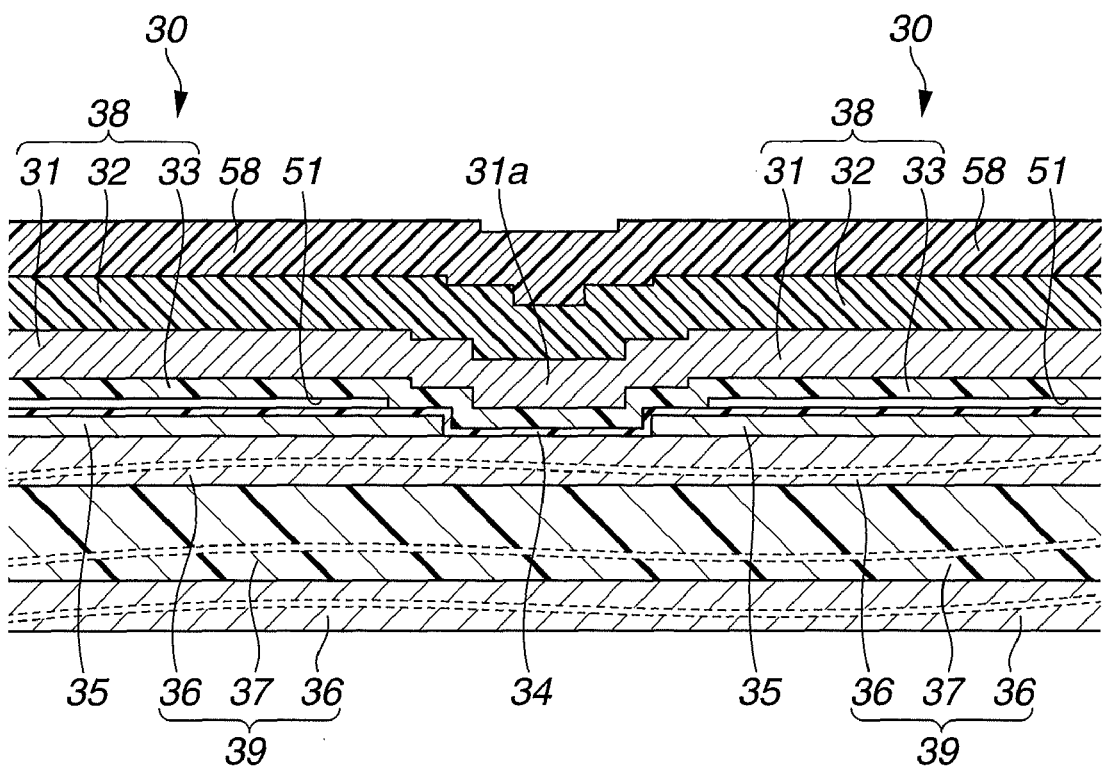
FIG. 7 is a partial cross-sectional view of the ultrasonic transducer cells taken along VII-VII line in FIG. 5.
Figure 8:
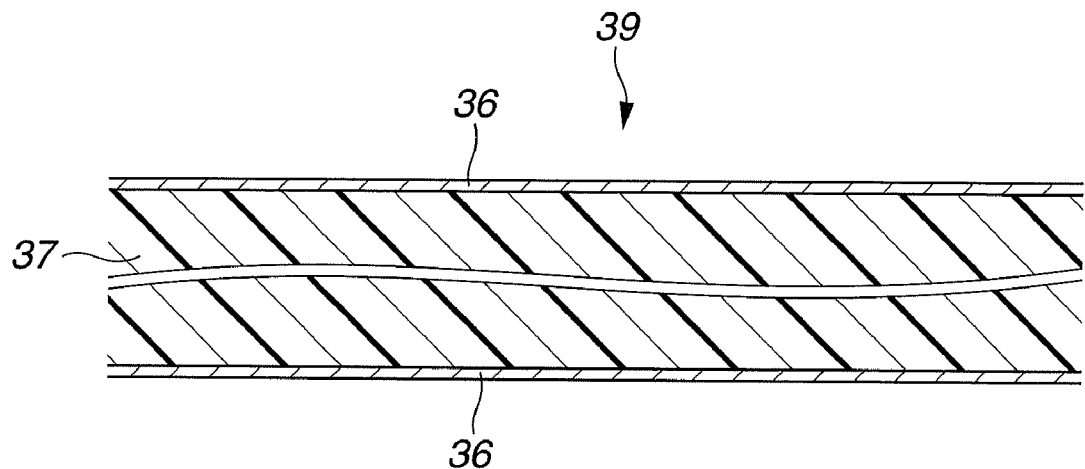
FIG. 8 is a cross-sectional view of a wafer with a thick oxide film.
Figure 9:
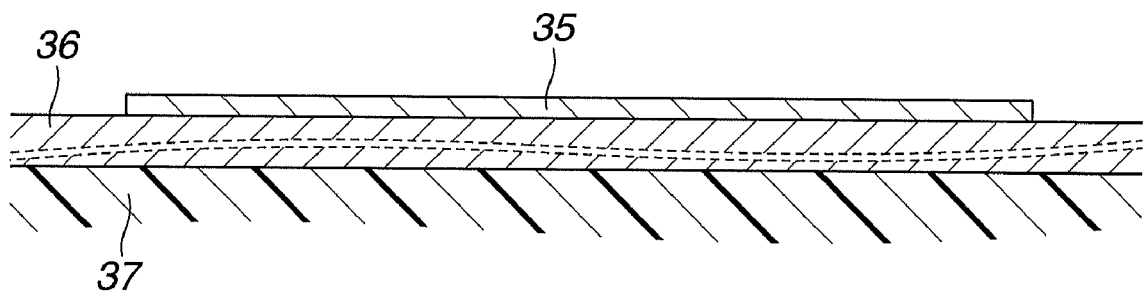
FIG. 9 is a cross-sectional view showing a fabrication process of ultrasonic transducer cells after lower electrodes are formed on the wafer with the thick oxide film.
Figure 10:
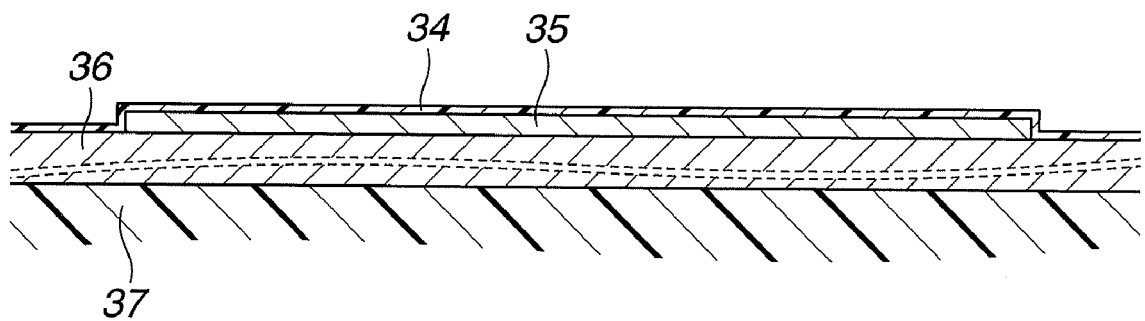
FIG. 10 is a cross-sectional view showing the fabrication process of ultrasonic transducer cells after a first insulating layer is formed.
Figure 11:
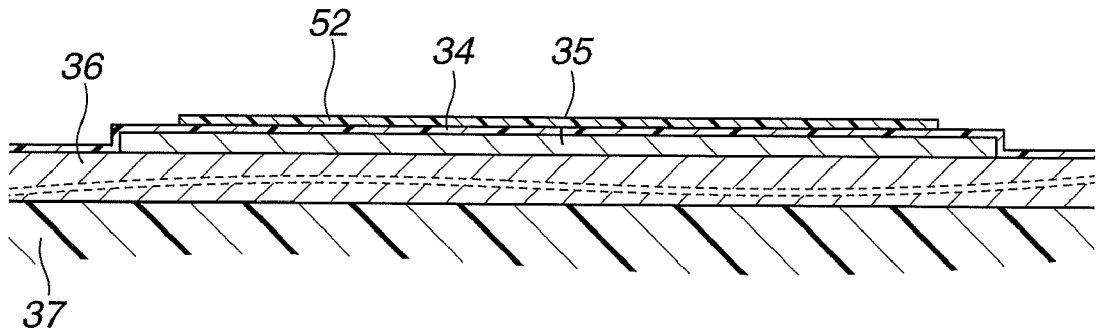
FIG. 11 is a cross-sectional view showing the fabrication process of ultrasonic transducer cells after a sacrificial layer is formed.
Figure 12:
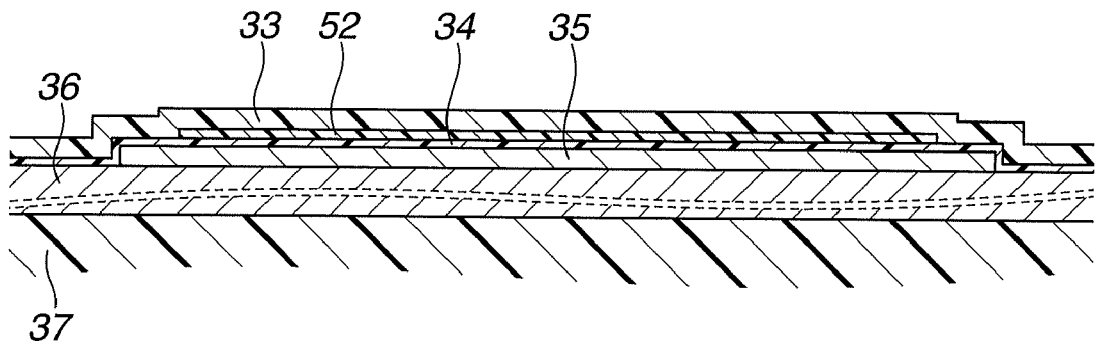
FIG. 12 is a cross-sectional view showing the fabrication process of ultrasonic transducer cells after a second insulating layer is formed.
Figure 13:
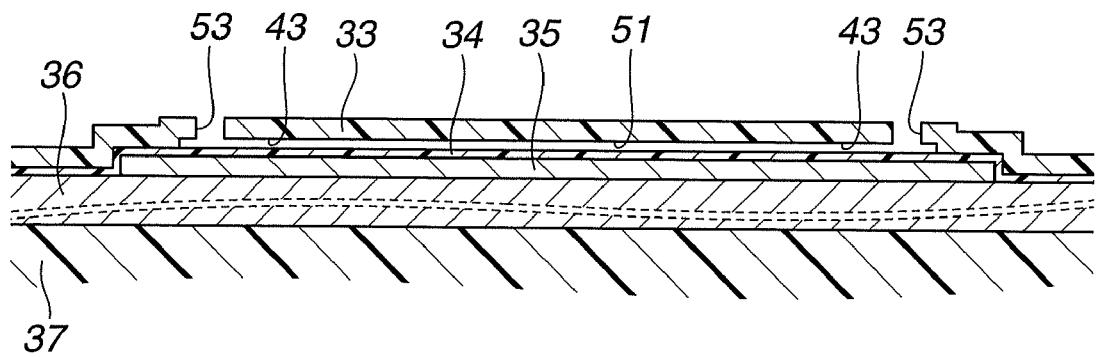
FIG. 13 is a cross-sectional view showing the fabrication process of ultrasonic transducer cells after sacrificial layer removal holes are formed and the sacrificial layer is removed.
Figure 14:
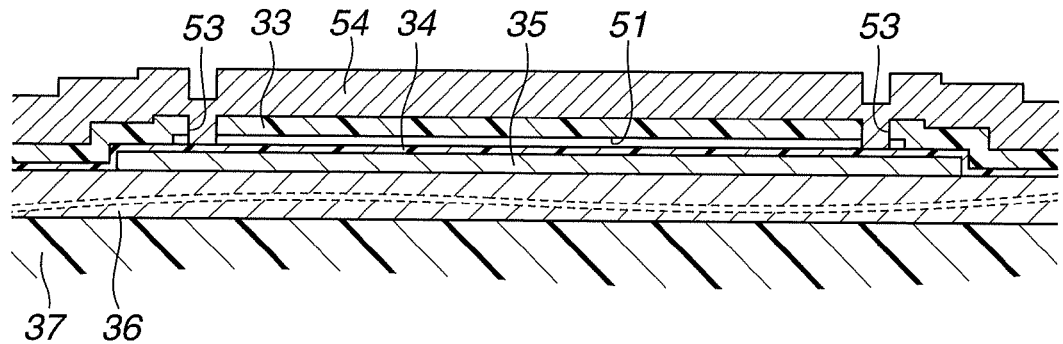
FIG. 14 is a cross-sectional view showing the fabrication process of ultrasonic transducer cells after an aluminum film is formed.
Figure 15:
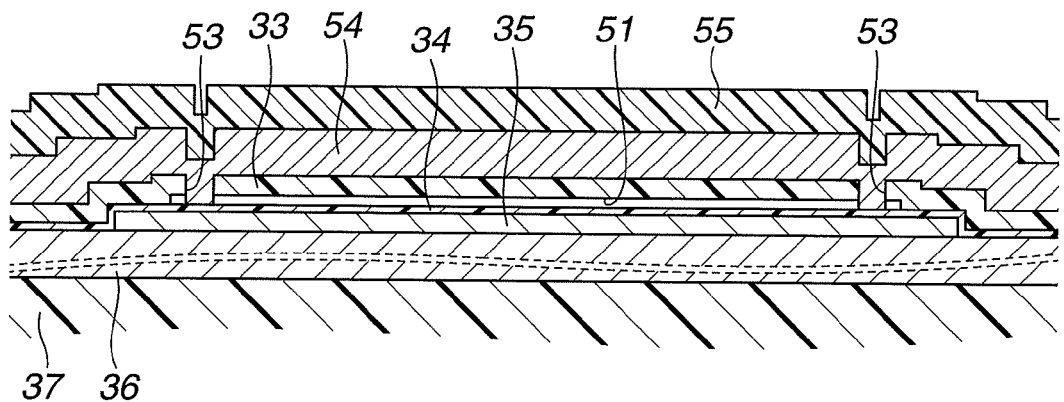
FIG. 15 is a cross-sectional view showing the fabrication process of ultrasonic transducer cells after an insulating film is formed.
Figure 16:
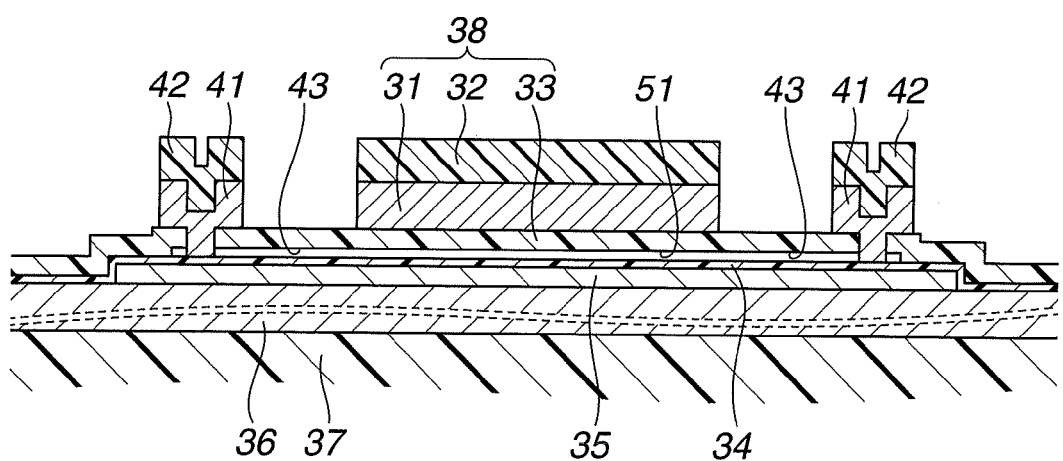
FIG. 16 is a cross-sectional view showing the fabrication process of ultrasonic transducer cells after upper electrodes covered from above with a third insulating layer and sealing portions covered from above with an insulating layer are formed by etching.
Figure 17:
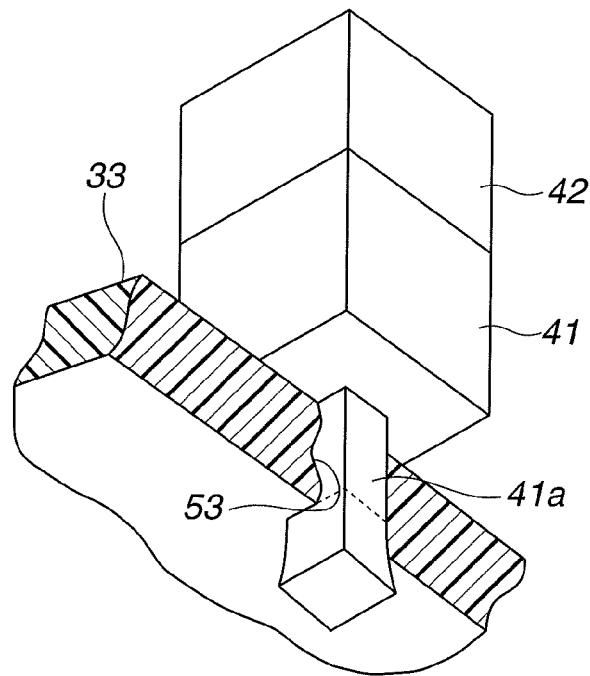
FIG. 17 is perspective view showing shape of the sealing portions which plug the sacrificial layer removal holes.
Figure 18:
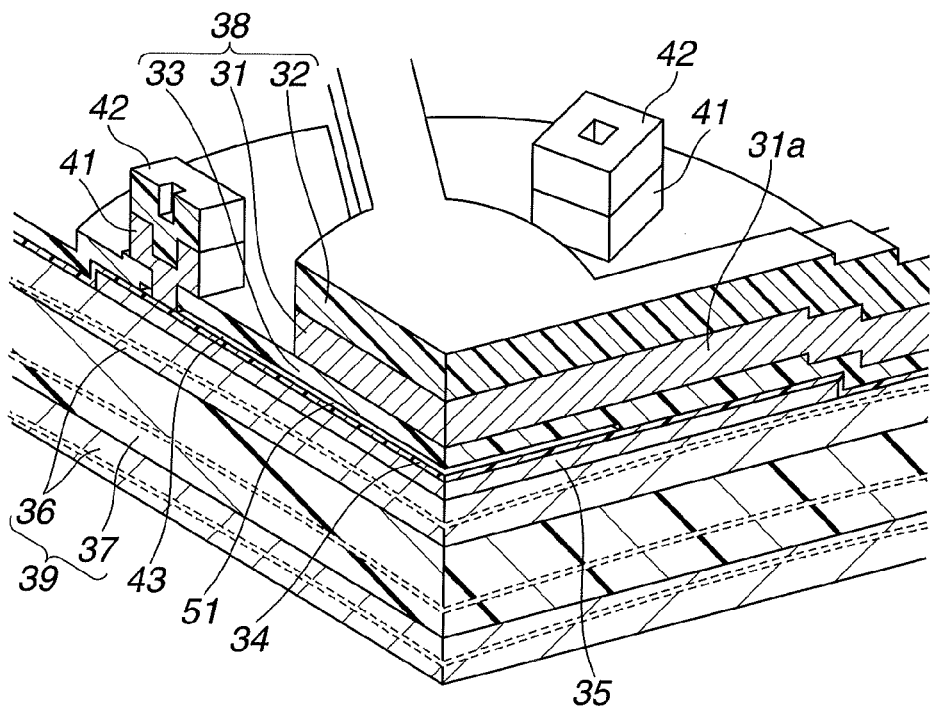
FIG. 18 is a perspective view showing a cross section obtained by cutting the ultrasonic transducer cells in FIG. 16 in two directions.
Figure 19:
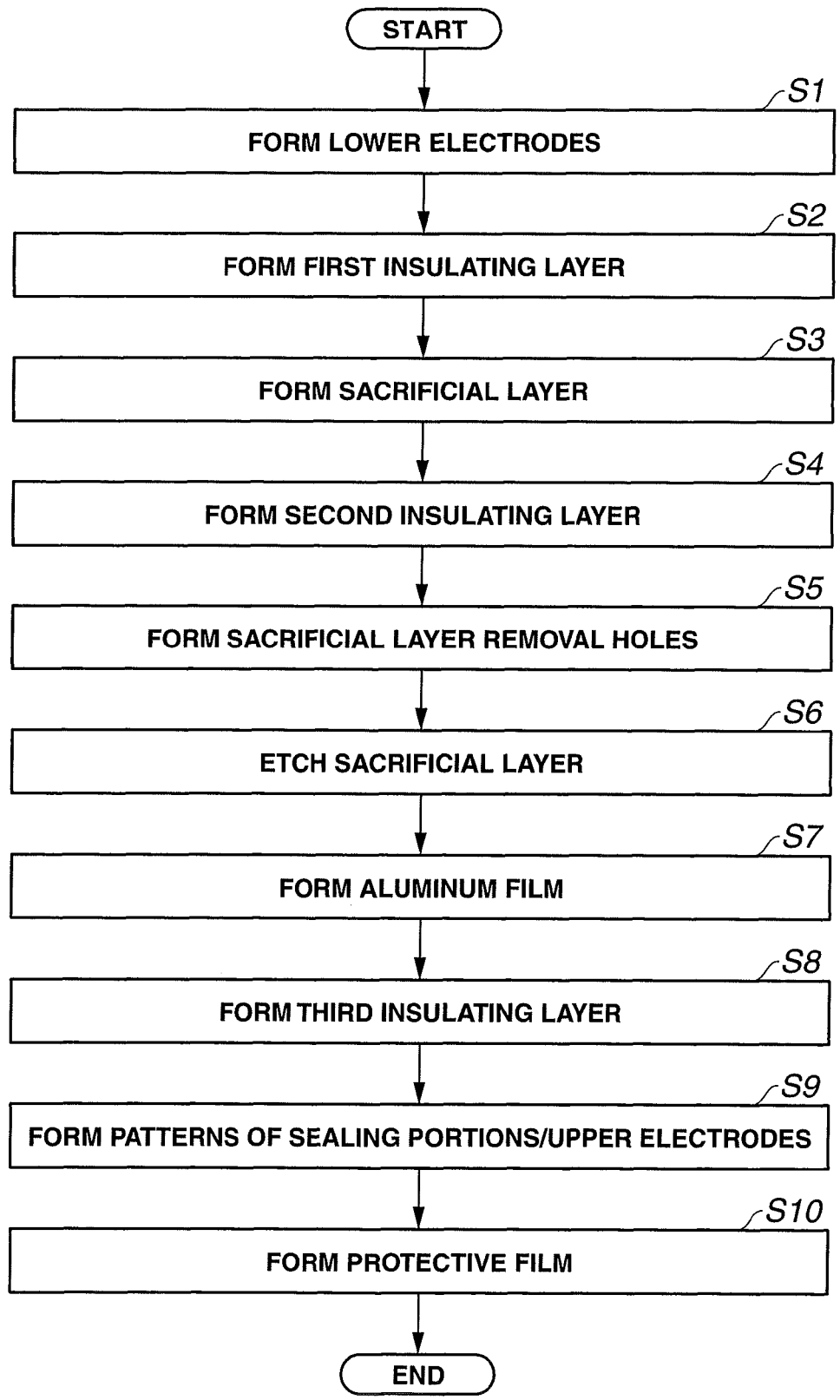
FIG. 19 is a flowchart showing a fabrication process of ultrasonic transducer cells.

FIG. 4 is a top view of an ultrasonic transducer, FIG. 5 is an enlarged view of encircled part V in FIG. 4, FIG. 6 is a cross-sectional view of ultrasonic transducer cells taken along VI-VI line in FIG. 5, FIG. 7 is a cross-sectional view of the ultrasonic transducer cells taken along VII-VII line in FIG. 5, FIG. 8 is a cross-sectional view of a wafer with a thick oxide film, FIG. 9 is a cross-sectional view showing a fabrication process of ultrasonic transducer cells after lower electrodes are formed on the wafer with the thick oxide film, FIG. 10 is a cross-sectional view showing the fabrication process of ultrasonic transducer cells after a first insulating layer is formed, FIG. 11 is a cross-sectional view showing the fabrication process of ultrasonic transducer cells after a sacrificial layer is formed, FIG. 12 is a cross-sectional view showing the fabrication process of ultrasonic transducer cells after a second insulating layer is formed, FIG. 13 is a cross-sectional view showing the fabrication process of ultrasonic transducer cells after sacrificial layer removal, namely, holes are formed and the sacrificial layer is removed, FIG. 14 is a cross-sectional view showing the fabrication process of ultrasonic transducer cells after an aluminum film is formed, FIG. 15 is a cross-sectional view showing the fabrication process of ultrasonic transducer cells after an insulating film is formed, FIG. 16 is a cross-sectional view showing the fabrication process of ultrasonic transducer cells after upper electrodes covered from above with a third insulating layer and sealing portions covered from above with an insulating layer are formed by etching, FIG. 17 is diagram showing shape of the sealing portions which plug the sacrificial layer removal holes, FIG. 18 is a perspective view showing a cross section obtained by cutting the ultrasonic transducer cells in FIG. 16 in two directions, and FIG. 19 is a flowchart showing a fabrication process of ultrasonic transducer cells. However, shapes of components, size ratios among the components, placement locations of the components, and the like of the ultrasonic transducer according to the present invention are not limited to those shown in the figures.

Each transducer element 25 has ultrasonic transducer cells 30 arranged at equal intervals in a grid-like fashion as shown in FIG. 4. Preferably, in each transducer element 25, the ultrasonic transducer cells 30 are electrically connected in parallel. As described later, the ultrasonic transducer cell 30 is a unit drive element which comprises at least a lower electrode, cavity placed on the lower electrode, and vibrating membrane placed on the cavity. The vibrating membrane according to the present invention comprises at least an insulating layer and an upper electrode placed on the insulating layer. Besides, an insulating layer or protective film may be placed on the upper electrode.

As shown in FIG. 5, the ultrasonic transducer cells 30 according to the present invention are communicated with each other via channels 43. Holes are provided in the channels 43 to remove a sacrificial layer during fabrication. Furthermore, the holes are sealed by sealing portions 41. According to the present invention, that part of the sealing portions 41 which enters the channels 43 is the same in cross-sectional shape as the holes. The cross section according to the present invention is a section along a direction parallel to a substrate 39. The sealing portions 41 according to the present invention do not deposit unnecessarily in the channels 43 and do not spread non-uniformly in the channels 43 unlike conventional sealing portions. This makes it possible to bring shapes of the cavities close to uniformity.

Shape of the ultrasonic transducer cells is not limited to the circular one shown in FIG. 5 and may be established as required according to purpose.

Upper electrodes 31 of the ultrasonic transducer cells 30 are electrically connected with each other via conductors 31a, where the upper electrodes 31 serve as return electrodes. Incidentally, in FIG. 5, the conductors 31a extend from four peripheral locations of each disk-shaped upper electrode 31 at angles of 45 degrees with respect to the adjacent channels 43, but the present invention is not limited to this.

Now, cross-sectional structure of the ultrasonic transducer cells 30 shown in FIG. 5 will be described in more detail with reference to FIGS. 6 and 7 in which the ultrasonic transducer cells 30 are cut along VI-VI line and VII-VII line.

As shown in FIG. 6, the ultrasonic transducer cell 30 according to the present invention mainly includes a lower electrode 35 formed on the substrate 39 and serving as the active electrode, a first insulating layer 34 formed on surfaces of the lower electrode 35 and the substrate 39, a cavity 51 formed above the lower electrode 35, a second insulating layer 33 formed on the cavity 51, and the upper electrode 31 formed on the second insulating layer 33. Also, as illustrated in FIG. 6 by way of example, a third insulating layer 32 may be formed on the upper electrode 31.

Incidentally, in the ultrasonic transducer cell 30 according to the present invention, the second insulating layer 33 and upper electrode 31 make up a vibrating membrane 38. Also, a third insulating layer 32, if formed, is also included in the vibrating membrane 38. Furthermore, if a protective film 58 is formed on a surface of the third insulating layer 32 as illustrated in FIG. 6 by way of example, the membrane 38 has four layers including the protective film 58. Details of the protective film will be described later.

Also, according to the present embodiment, the cavity 51 provides a damping layer for the membrane 38. Regarding terms "upper" and "lower," according to the present embodiment, an ultrasonic scanning region is regarded to be located on an upper side of generated ultrasonic vibration.

The cavities 51 are communicated with the channels 43 which are used for the removal of the sacrificial layer when forming the cavities 51 from the first insulating layer 34 and second insulating layer 33. Sacrificial layer removal holes for use to introduce a chemical agent or gas to dissolve the sacrificial layer are sealed by sealing portions 41. Incidentally, shape of the sacrificial layer removal holes is not limited to a quadrangular prism illustrated in FIG. 6 by way of example, and may be, for example, cylindrical.

As illustrated in FIG. 6 by way of example, preferably, an insulating film 42 is formed on the sealing portions 41 to keep the cavities 51 under vacuum. Incidentally, according to the present embodiment, the insulating film 42 provides second sealing portions and thus the sealing portions 41 provide first sealing portions.

In each transducer element 25, the upper electrode 31 of each ultrasonic transducer cell 30 and the conductors 31a are formed integrally as shown in FIG. 7, thereby electrically connecting adjacent upper electrodes 31. The third insulating layer 32 also covers the conductors 31a. Furthermore, a surface of the transducer element 25 on which a plurality of the ultrasonic transducer cells 30 configured as described above are arranged is covered with the protective film 58.

There is no particular limit on the substrate 39 on which the ultrasonic transducer cells 30 according to the present invention are formed, but a wafer with a thick oxide film can be used, for example. The wafer with a thick oxide film according to the present invention is a wafer whose surface is coated with an oxide film. According to the present embodiment, for example, a silicon substrate 37 with a silicon thermal oxide film 36 formed on a surface is used as the wafer with a thick oxide film. There is no particular limit on thickness of the silicon substrate 37, but preferably the thickness is 100 to 600 μm and more preferably 200 to 300 μm. There is no particular limit on thickness of the silicon thermal oxide film, but preferably the thickness is 5 to 25 μm and more preferably 10 to 20 μm.

The lower electrodes 35 formed on one surface of the substrate 39 is made of a conductive material such as metal or semiconductor. More specifically, molybdenum (Mo) is used for the lower electrodes 35. There is no particular limit on thickness of the lower electrodes, but preferably the thickness is 0.1 to 0.5 μm and more preferably 0.2 to 0.4 μm. Incidentally, although not illustrated, the lower electrodes 35 of the ultrasonic transducer cells 30 in the same transducer element 25 are electrically connected with each other.

There is no particular limit on thickness of the first insulating layer 34 which covers the surfaces of the lower electrodes 35 and the substrate 39, but preferably the thickness is 0.10 to 0.20 μm and more preferably 0.15 μm. There is no particular limit on material of the first insulating layer, but SiN is a possible choice. The first insulating layer 34 protects the lower electrodes 35 from the chemical agent or gas for etching as well as serves as an insulating film.

There is no particular limit on size of the cavities 51, but, for example, a cylinder 40 μm in diameter and 0.2 μm in cavity height is a possible choice. There is no particular limit on thickness of the second insulating layer 33, but preferably the thickness is 0.20 to 0.50 μm and more preferably 0.3 to 0.45 μm. There is no particular limit on material of the second insulating layer, and SiN is a possible choice. As in the case of the first insulating layer 34, the second insulating layer 33 provides a film of the membrane 38 to vibrate as well as serves as an electrical insulating film.

There is no particular limit on thickness of the upper electrodes 31, but preferably the thickness is 0.3 to 1.2 μm and more preferably 0.5 to 1.0 μm. There is no particular limit on material of the upper electrodes 31, but aluminum is a possible choice. Preferably, the conductors 31a formed integrally with the upper electrodes 31 are made of the same material as the upper electrodes 31. There is no particular limit on thicknesses of the third insulating layer 32, the insulating film 42 which can be formed on the sealing portions 41, and the protective film 58, but preferably the thicknesses are 0.2 to 1.5 μm and more preferably 0.5 to 1.0 μm. There is no particular limit on material of the insulating film and protective film, but SiN is a possible choice.

Next, with reference to FIGS. 8 to 18 and steps (S) in a flowchart of FIG. 19, description will be given of an example of a fabrication method of the transducer element 25 which includes a plurality of the ultrasonic transducer cells 30 according to the present embodiment, the ultrasonic transducer cells 30 being configured as described above. Incidentally, although FIGS. 8 to 18 illustrate a cross section of a single ultrasonic transducer cell 30, the fabrication method described below can be applied to a process for forming a plurality of transducer elements 25 containing fine diaphragm-like ultrasonic transducers on a single substrate 39 using a micromachining technique. The ultrasonic transducer formed using the micromachining technique is called c-MUT (Capacitive Micromachined Ultrasonic Transducer). The use of the micromachining technique makes it possible to form the c-MUT without using lead (Pb).

First, as shown in FIG. 8, a silicon substrate 37 with a thick silicon oxide film ($SiO_2$ film) formed on both faces is prepared as the substrate 39 and a film of conductive material is formed on one face of the substrate 39. Then, a pattern of the lower electrodes 35 is formed by partially removing the film of conductive material as shown in FIG. 9 (S1). The preferable thickness and material of the silicon oxide film have been described above. There is no particular limit on a method for forming the film of conductive material, but a sputtering process, for example, is a possible choice. Also, there is no particular limit on a method for partially removing the film of conductive material, but etching by means of a photolithography process is a possible choice.

As shown in FIG. 10, a next step involves forming a film of insulative material and thereby forming the first insulating layer 34 on the face of the substrate 39 on which the lower electrodes 35 have been formed (S2). There is no particular limit on the insulative material, but SiN is a possible choice. There is no particular limit on a method for forming the film of insulative material, but a CVD process (Chemical Vapor Deposition), for example, is a possible choice.

As shown in FIG. 11, a next step involves forming a film of sacrificial layer material on the first insulating layer 34, partially removing the sacrificial layer material, and thereby forming a pattern of a sacrificial layer 52 (S3). The pattern formation defines the shapes and sizes of the cavities 51 and channels 43. There is no particular limit on thickness of the sacrificial layer material, but preferably the thickness is 0.05 to 0.3 μm and more preferably 0.05 to 0.15 μm. Also, there is no particular limit on the sacrificial layer material, but possible choices include, for example, phosphorus doped low-temperature silicone dioxide (PSG), silicon dioxide ($SiO_2$), polysilicon, and metal.

As shown in FIG. 12, a next step involves forming a film of insulating material on a top face of the first insulating layer 34 on which the sacrificial layer 52 has been formed and thereby forming the second insulating layer 33 (S4).

Then, sacrificial layer removal holes 53 for use to introduce a chemical agent or gas to remove the sacrificial layer 52 is formed at predetermined locations on the second insulating layer 33 on the sacrificial layer 52 (S5). There is no particular limit on a method for forming the sacrificial layer removal holes, but a photolithography process may be used.

Next, according to the present embodiment, a next step involves removing the sacrificial layer 52 using the chemical agent or gas through the sacrificial layer removal holes 53 (S6). There is no particular limit on the chemical agent or gas, which thus can be selected as required depending on sacrificial layer material, first insulating layer material, or second insulating layer material. For example, if phosphorus doped low-temperature silicone dioxide is used as the sacrificial layer material and the first insulating layer and second insulating layer are made of SiN, hydrogen fluoride liquid can be used as the chemical agent. Hydrogen fluoride dissolves phosphorus doped low-temperature silicone dioxide, but does not easily dissolve SiN, and thus the shape of the cavities 51 can be made uniform easily.

Consequently, the sacrificial layer 52 is removed by the chemical agent and gaps are formed between the first insulating layer 34 and second insulating layer 33, forming the cavities 51 and channels 43 such as shown in FIG. 13. Also, the channels 43 are open through the sacrificial layer removal holes 53.

A next step involves depositing conductive material and thereby forming a conductive film 54 on a top face of the second insulating layer 33 by the sputtering process or vacuum evaporation as shown in FIG. 14 (S7). The conductive film 54 is deposited so as to plug the sacrificial layer removal holes 53. There is no particular limit on the conductive material, and possible choices include, for example, metal materials such as aluminum (AL), molybdenum (Mo), and titanium (Ti).

Possible methods for forming the conductive film 54 include the sputtering process and vacuum evaporation as described above, and the sputtering process is more preferable.

A next step involves forming a film of insulative material on a top face of the conductive film 54 and thereby forming an insulating film 55 which is to serve as the third insulating layer as shown in FIG. 15 (S8). There is no particular limit on the insulative material, but SiN, for example, is a possible choice. There is no particular limit on a film formation method, but a CVD process, for example, is a possible choice.

A next step involves partially removing the conductive film 54 together with insulating film 55 and thereby forming patterns of the upper electrodes 31 covered from above with the third insulating layer 32 and sealing portions 41 covered from above with the insulating film 42 as shown in FIG. 16 (S9). There is no particular limit on a method for removing the insulating film 55 and conductive film 54, but a photolithography process is a possible choice. Incidentally, the pattern of the upper electrodes 31 is formed in such a way that adjacent upper electrodes 31 will be electrically connected with each other via the conductors 31a.

In this state, the sealing portions 41 seal the sacrificial layer removal holes 53, where that part of the sealing portions 41 which enters the cavities is the same in cross-sectional shape as the sacrificial layer removal holes 53.

This is because the sputtering process and vacuum evaporation can move particles to be deposited in straight lines. This prevents the particles from spreading in the channels 43, much less from spreading to and depositing in the cavities 51, and from obstructing gap formation in the cavities 51.

Also, as shown in FIG. 18, the membrane 38 in each ultrasonic transducer cell 30 according to the present invention includes the second insulating layer 33, upper electrode 31, and third insulating layer 32. Finally, the protective film 58 (see FIGS. 6 and 7) is formed on the surface of the transducer element 25 (S10). There is no particular limit on a method for forming the protective film, but a CVD process, for example, is a possible choice.

Incidentally, a biocompatible outer skin such as a parylene film may be formed on the protective film 58. Since a membrane serving as the vibrating membrane of each ultrasonic transducer cell 30 is made up of the biocompatible outer skin, protective film 58, third insulating layer 32, upper electrode 31, and second insulating layer 33, their dimensions in a thickness direction are determined as required depending on their mechanical vibration and electrical characteristics.

As described above, according to the present embodiment, since the sealing portions 41 which plug the sacrificial layer removal holes 53 used to etch the sacrificial layer 52 for use to form the cavities 51 in the ultrasonic transducer cells 30 is formed by the sputtering process or vacuum evaporation, posts 41a of the sealing portions 41 can be made to deposit only directly under the sacrificial layer removal holes 53. Consequently, specimen particles of the sealing portions 41 do not deposit in the cavities 51, which makes it possible to form the cavities 51 in a stable manner.

Also, since the CVD process is not used for formation of the sealing portions 41, the sealing portions 41 do not spread to the channels 43 or cavities 51 and thus the sacrificial layer removal holes 53 can be made larger. This makes it easier to etch the sacrificial layer 52 and possible to increase the etching rate. Also, since the first insulating layer 34 and second insulating layer 33 are not etched unnecessarily, the cavities 51 can be formed in a stable manner.

Furthermore, since the channels 43 communicated with the cavities 51 can be formed in straight lines and the sacrificial layer removal holes 53 can be formed near the cavities 51, it is possible increase the etching rate and the cavities 51 can be formed in a stable manner similarly to the above.

Incidentally, the conventional CVD process, which performs film formation processes at temperatures of 700 to 800 degrees, can adversely affect the shape of the cavities 51 formed between the first insulating layer 34 and second insulating layer 34 and 33, but the sputtering process, which can perform film formation processes at temperatures of 200 to 300 degrees, is less likely to adversely affect the shape of the cavities 51.

Consequently, ultrasonic vibration of the ultrasonic transducer cells 30 by means of the cavities 51 becomes uniform, stabilizing ultrasonic vibration characteristics of the transducer element 25

Also, since the channels 43 can be formed in straight lines, reducing distance between adjacent ultrasonic transducer cells 30, a plurality of the ultrasonic transducer cells 30 can be arranged at high density, making it possible to produce a transducer element 25 which has highly accurate vibration characteristics. Thus, the transducer element 25 according to the present embodiment can deliver ultrasonic vibration to an ultrasonic scanning region with high accuracy. Consequently, internal bodily conditions can be acquired as high-accuracy images from echo signals.

That is, the present embodiment, which does not have limits on the shape and length of the channels 43 or size of the sacrificial layer removal holes 53, drastically increases the degree of freedom of array design of the ultrasonic transducer cells 30 in each transducer element 25.

Furthermore, the present embodiment, which uses the sputtering process, makes it possible to use low-melting-point metals such as aluminum (Al) for the upper electrodes 31 and sealing portions 41, increasing choice of available materials. Also, the use of the same material, aluminum (Al), in this case, for the upper electrodes 31 and sealing portions 41 makes it possible to simplify fabrication processes.

Second Embodiment

Next, a second embodiment will be described with reference to FIGS. 20 and 23.

Figure 20:
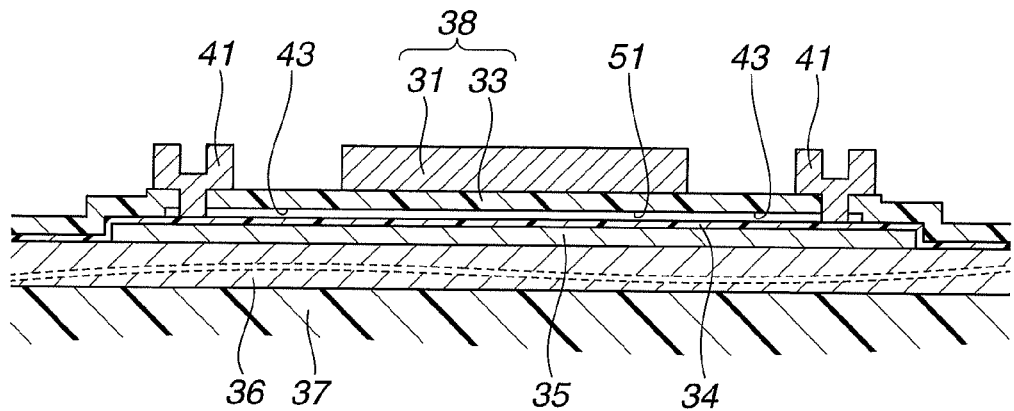
FIG. 20 is a cross-sectional view showing a fabrication process of ultrasonic transducer cells according to a second embodiment after upper electrodes and sealing portions are formed by etching.
Figure 21:
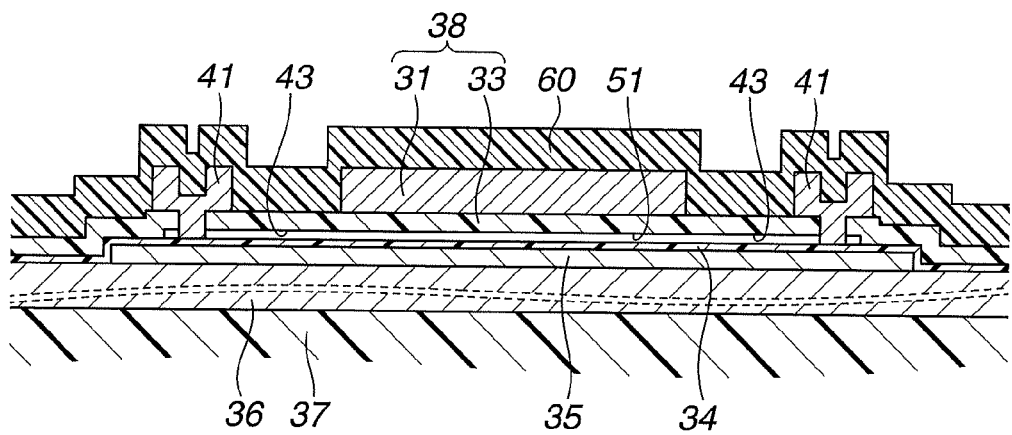
FIG. 21 is a cross-sectional view showing the fabrication process of ultrasonic transducer cells after a protective film is formed.
Figure 22:
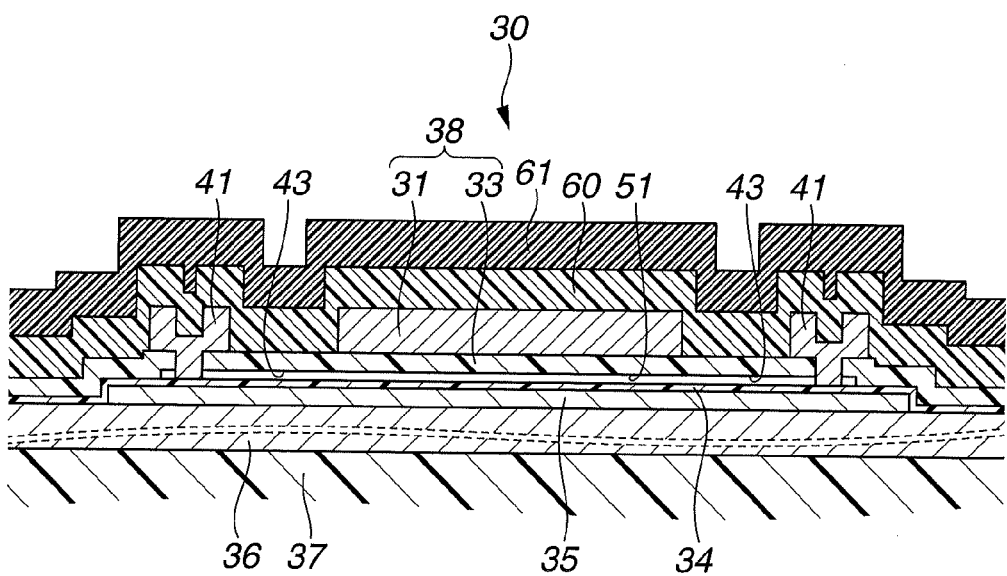
FIG. 22 is a cross-sectional view showing the fabrication process of ultrasonic transducer cells after a parylene film is formed.
Figure 23:
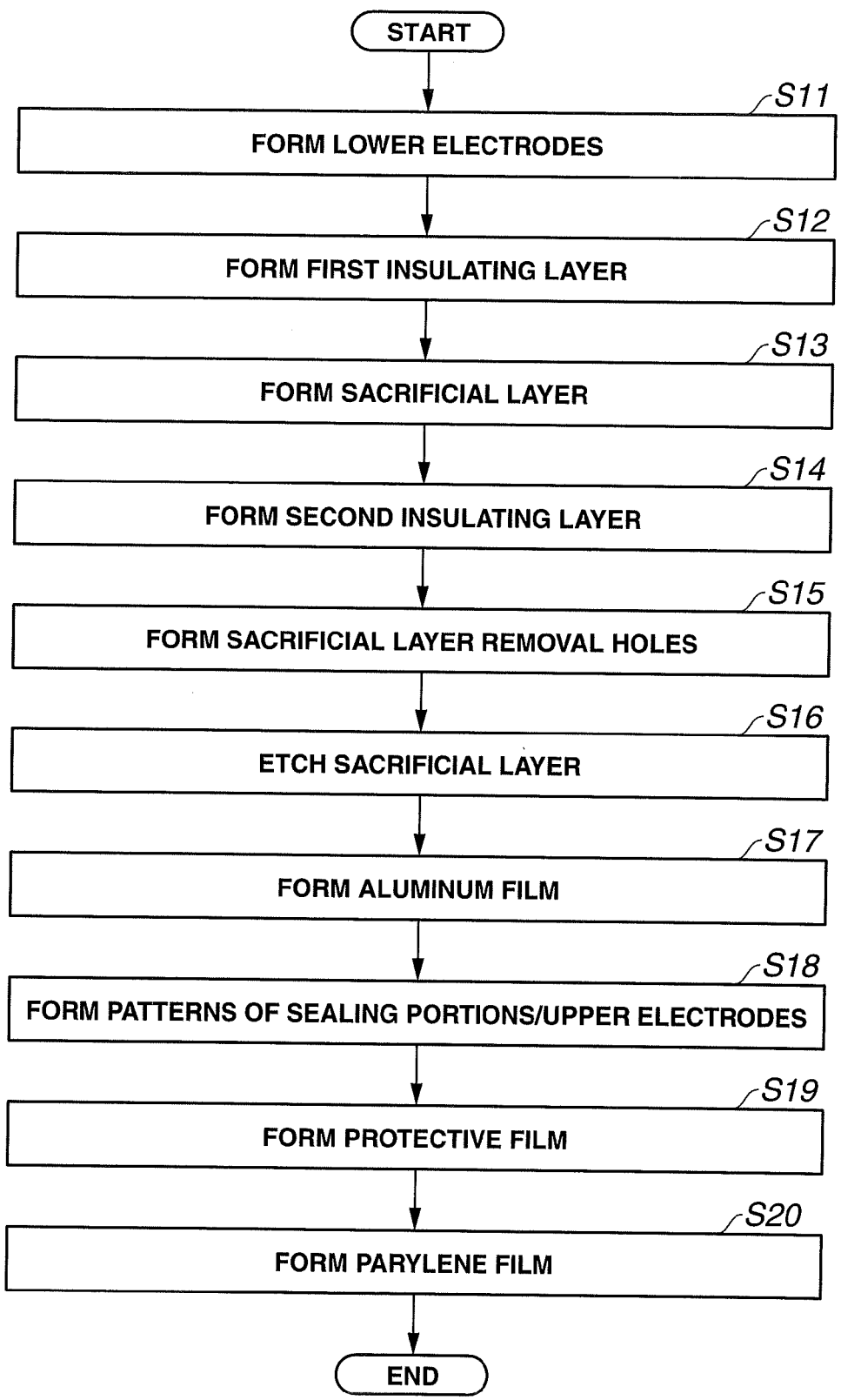
FIG. 23 is a flowchart showing a fabrication process of ultrasonic transducer cells.

FIGS. 20 and 23 concern the second embodiment, where FIG. 20 is a cross-sectional view showing a fabrication process of ultrasonic transducer cells after upper electrodes and sealing portions are formed by etching, FIG. 21 is a cross-sectional view showing the fabrication process of ultrasonic transducer cells after a protective film is formed, FIG. 22 is a cross-sectional view showing the fabrication process of ultrasonic transducer cells after a parylene film is formed, FIG. 23 is a flowchart showing a fabrication process of ultrasonic transducer cells.

In the following description, the same components as those in the first embodiment will be denoted by the same reference numerals as the corresponding components in the first embodiment, and description thereof will be omitted and only differences from the first embodiment will be described.

The fabrication method of the transducer element 25 which includes a plurality of the ultrasonic transducer cells 30 according to the present embodiment will be described with reference to 20 to 22 and steps (S) in a flowchart of FIG. 23. Steps S11 to S17 in the flowchart of FIG. 23 are identical to Steps S1 to S7 in the flowchart of FIG. 17 according to the first embodiment, and thus description thereof will be omitted and the fabrication method according to the present embodiment will be described beginning with Step S18 in FIG. 23.

According to the present embodiment, after formation of the conductive film 54 (see FIG. 14) in Step S17, which is the same as Step S7 according to the first embodiment, patterns of the upper electrodes 31 and sealing portions 41 are formed on the conductive film 54 by the photolithography process as shown in FIG. 20 (S18).

A next step involves forming an insulative film on the transducer element 25 as shown in FIG. 21 and thereby forming a protective film 60 (S19). There is no particular limit on a method for forming the protective film, but a CVD process is a possible choice.

Finally, a biocompatible outer skin is formed on the protective film 60 (S20). There is no particular limit on material of the outer skin, but parylene is a possible choice (poly-para-xylene).

Being configured as described above, the ultrasonic transducer cells 30 according to the present embodiment offers the same advantages as those of the first embodiment while eliminating steps formed by the third insulating layer 32 and insulating film 42 in the configuration of the ultrasonic transducer cells 30 according to the first embodiment shown in FIG. 6. This provides a flattened structure by minimizing irregularities on the surface of the transducer element 25 caused by the upper electrodes 31 and sealing portions 41.

Incidentally, according to the first and second embodiments, since the protective film 58 or 60 of silicon nitride (SiN) is formed on the upper electrodes 31 using the CVD process which provides good coverage in terms of deposition, it is possible to improve electrical isolation of the upper electrodes 31 as well as to improve practical ability of the ultrasonic endoscope 1 to withstand cleaning, disinfection, sterilization, and other operations peculiar to the ultrasonic endoscope 1 which is a medical device.

Figure 24:
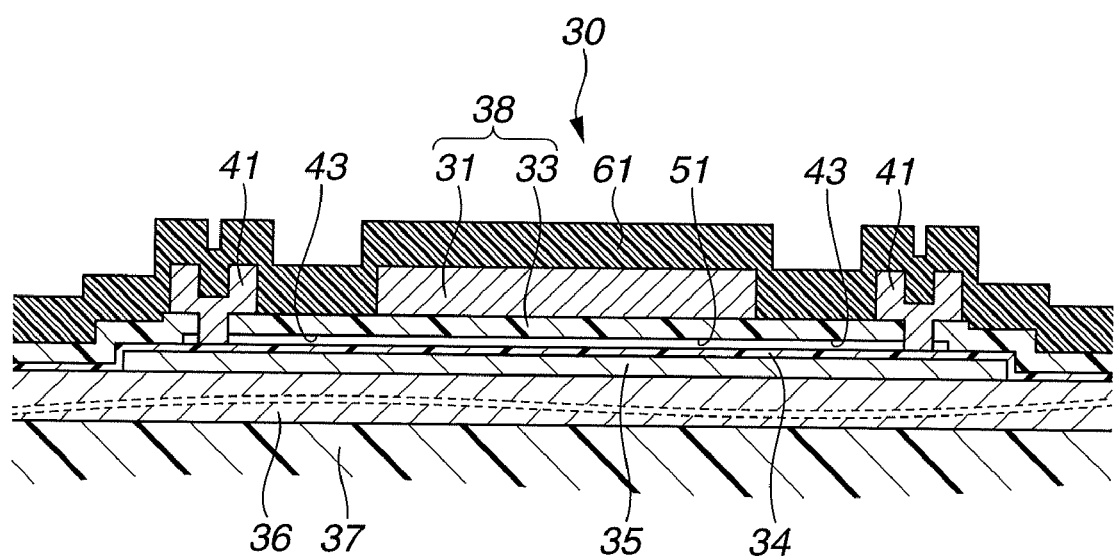
FIG. 24 is a cross-sectional view of ultrasonic transducer cells according to a variation.

Incidentally, as shown in FIG. 24, only a parylene film 61, for example, may be formed on the surface of the transducer element 25 as a biocompatible outer skin without forming a protective film. This configuration can simplify fabrication processes. Addition of fluorine can make the parylene film 61 less prone to contamination with protein or the like and ensures that cleaning, disinfection, sterilization, and other operations will be carried out more reliably.

The invention described above by way of the embodiments is not limited to the embodiments and variations thereof. Numerous variations can be made at implementation levels without departing from the spirit of the present invention. Furthermore, the above embodiments include inventions at various stages, and various inventions can result from proper combinations of multiple components disclosed herein.

For example, even if some of the components of the embodiments are removed, as long as the problems to be solved by the invention can be solved and the advantages of the invention are available, the resulting configuration can constitute an invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic transducer fabrication method using a micromachining technique, comprising the steps of:
    depositing a conductive material on an insulating layer on a surface of a substrate, partially etching the conductive material, and thereby forming lower electrodes;
    depositing an insulating material so as to cover the lower electrodes and the insulating layer and thereby forming a first insulating layer;
    depositing a sacrificial material on the first insulating layer, performing etching, and thereby creating two or more cavities and a channel-shaped sacrificial layer which communicates the cavities with each other;
    depositing an insulating material on the first insulating layer and the sacrificial layer and thereby forming a second insulating layer;
    partially etching the second insulating layer formed on the channel-shaped sacrificial layer and thereby forming holes;
    etching and removing the sacrificial layer through the holes and thereby forming the cavities and the channels;
    depositing a conductive material on the second insulating layer by a vacuum evaporation or a sputtering process so as to plug the holes, thereby forming a conductive film;
    partially etching the conductive film and thereby forming upper electrodes and sealing portions which plug the holes; and forming a protective film on the second insulating layer using a protective material so as to cover the upper electrodes and the sealing portions.

2. The ultrasonic transducer fabrication method according to claim 1, further comprising a step of depositing an insulating material on the conductive material, partially etching the insulating material, and thereby forming the upper electrodes covered from above by a third insulating layer and the sealing portions covered from above by an insulating film after the step of depositing the conductive material on the second insulating layer, by the vacuum evaporation or the sputtering process so as to plug the holes.

3. The ultrasonic transducer fabrication method according to claim 2, wherein the third insulating layer and the insulating film are formed of the insulating material by the chemical vapor deposition.

4. The ultrasonic transducer fabrication method according to claim 1, further comprising the step of further depositing a conductive material by Chemical Vapor Deposition to form another conductive film after depositing the conductive material by the sputtering process or the vacuum evaporation.

* * * * *